(12) United States Patent
Narasimhan et al.

(10) Patent No.: US 11,026,632 B2
(45) Date of Patent: Jun. 8, 2021

(54) DETERMINING RESPIRATORY RATE VIA IMPEDANCE PNEUMOGRAPHY

(75) Inventors: Ravi Narasimhan, Sunnyvale, CA (US); Nima Ferdosi, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 630 days.

(21) Appl. No.: 13/452,632

(22) Filed: Apr. 20, 2012

(65) Prior Publication Data
US 2013/0281875 A1 Oct. 24, 2013

(51) Int. Cl.
*A61B 5/08* (2006.01)
*A61B 5/00* (2006.01)

(52) U.S. Cl.
CPC ............ *A61B 5/725* (2013.01); *A61B 5/0809* (2013.01); *A61B 5/0816* (2013.01)

(58) Field of Classification Search
CPC ............................ A61B 5/0809; A61B 5/0816
USPC .................................. 600/484, 529, 534, 536
See application file for complete search history.

(56) References Cited

U.S. PATENT DOCUMENTS

| | | |
|---|---|---|
| 6,494,829 B1 | 12/2002 | New, Jr. et al. |
| 7,822,471 B2 | 10/2010 | Bowers |
| 2004/0267143 A1 | 12/2004 | Sweeney |
| 2008/0009757 A1 | 1/2008 | Tsoglin et al. |
| 2009/0264792 A1* | 10/2009 | Mazar .................. A61B 5/0531 600/547 |
| 2010/0292568 A1 | 11/2010 | Droitcour et al. |
| 2011/0245711 A1 | 10/2011 | Katra et al. |
| 2012/0016255 A1* | 1/2012 | Masuo ................ A61B 5/0809 600/547 |
| 2012/0029307 A1 | 2/2012 | Paquet et al. |

OTHER PUBLICATIONS

PCT International Search Report and Written Opinion of the International Searching Authority, dated Jul. 5, 2013, application No. PCT/US2013/033167.
A. K. Gupta, "Respiration rate measurement based on impedance pneumography," Texas Instruments Application Report SBAA181, Feb. 2011.
S. Luo, V. X. Afonso, J. G. Webster and W. J. Tompkins, "The electrode system in impedance-based ventilation measurement," IEEE Trans. Biomedical Eng., vol. 39, No. 11, pp. 1130-1141, Nov. 1992.
S. P. Kelkar, N. D. Khambete and S. S. Agashe, "Development of movement artefacts free breathing monitor," J. Instrum. Soc. India, 38(1): 34-43, 2008.

* cited by examiner

*Primary Examiner* — Puya Agahi
(74) *Attorney, Agent, or Firm* — Brundidge & Stanger, P.C.

(57) ABSTRACT

A method and system for determining a respiratory rate of a user are disclosed. The method comprises measuring a differential voltage across first and second electrodes of a sensor device coupled to the user. The method includes sampling the differential voltage using an analog-to-digital converter to produce an output signal. The method includes processing the output signal to detect a breath of the user based on a positive voltage transition through a midpoint, wherein the breath of the user is utilized to determine the respiratory rate of the user.

18 Claims, 4 Drawing Sheets

DETERMINING RESPIRATORY RATE VIA IMPEDANCE PNEUMOGRAPHY

FIELD OF THE INVENTION

The present invention relates to sensor devices, and more particularly, to a sensor device utilized to determine respiratory rate via impedance pneumography.

BACKGROUND

A person's respiratory rate measures the number of breaths taken within a predetermined time period, typically 60 seconds. A normal respiratory rate is termed eupnea, an increased respiratory rate is termed tachypnea, and a lower than normal respiratory rate is termed bradypnea. A person's age, physical condition, and medical history all have a direct effect on the ability to maintain eupnea.

Monitoring a person's respiratory rate is crucial to checking for any potential medical conditions and maintaining the overall health of a person. Conventional methods of testing a person's respiratory rate include measuring each breath when the person is at rest over a predetermined time period by counting how many times the person's chest rises. Devices such as stethoscopes are often utilized by doctors to assist as well. However, these conventional methods are inefficient, costly and require time consuming analysis to arrive at the person's respiratory rate.

These issues limit the continuous monitoring of a person's respiratory rate. Therefore, there is a strong need for a cost-effective solution that overcomes the above issues by non-invasively calculating respiratory rate in real-time using sensor devices. The present invention addresses such a need.

SUMMARY OF THE INVENTION

A method and system for determining a respiratory rate of a user are disclosed. In a first aspect, the method comprises measuring a differential voltage across first and second electrodes of a sensor device coupled to the user. The method includes sampling the differential voltage using an analog-to-digital converter to produce an output signal. The method includes processing the output signal to detect a breath of the user based on a positive voltage transition through a midpoint, wherein the breath of the user is utilized to determine the respiratory rate of the user.

In a second aspect, the system comprises a sensor device that includes first and second electrodes coupled to the user. The sensor device measures a differential voltage across the first and second electrodes. An analog-to-digital converter is coupled to the sensor device and samples the differential voltage to produce an output signal. The sensor device processes the output signal to detect a breath of the user based on a positive voltage transition through a midpoint, wherein the breath of the user is utilized to determine the respiratory rate of the user.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to sensor devices, and more particularly, to a sensor device utilized to determine respiratory rate via impedance pneumography. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A method and system in accordance with the present invention allows for the measurement of a user's respiratory rate using a sensor device via impedance pneumography. One of ordinary skill in the art readily recognizes that a variety of sensor devices can be utilized for the impedance pneumography including portable wireless sensor devices with embedded circuitry and that would be within the spirit and scope of the present invention. By connecting a sensor device to the user through two or more skin contacting sensor nodes or electrodes and stimulating these sensor nodes with an electrical signal through a known impedance by a differential voltage generator, a resultant electrical output signal across the sensor nodes is detected by the sensor device. The resultant electrical output signal is sampled using an analog-to-digital converter and then processed by the sensor device using digital signal processing to determine the user's respiratory rate.

In one embodiment, the resultant electrical output signal is a differential voltage ($V_{body}$) measured across two or more electrodes of the sensor device that is coupled to a user. One of ordinary skill in the art readily recognizes that the sensor device can be coupled to the user using a variety of mechanisms including but not limited to an adhesive layer on the bottom of the sensor device that is in a patch form factor and that would be within the spirit and scope of the present invention. The differential voltage is measured by injecting an input voltage ($V_{in}$) through a known impedance ($Z_{in}$) and through the two or more electrodes coupled to the user's body which has an unknown body impedance ($Z_{body}$). Given that $V_{in}$ and $Z_{in}$ are known values and that the differential voltage ($V_{body}$) across $Z_{body}$ can be measured by the sensor device, $Z_{body}$ can be calculated per the following equation:

$$Z_{body} = (V_{body}/(V_{in} - V_{body})) \times Z_{in}.$$

In one embodiment, the change in the calculated $Z_{body}$ value is utilized to measure respiration rate and respiration depth. When a person inhales and air fills up the lungs, the impedance across the person's lungs increases. When the person exhales and there is less air in the lungs, the impedance across the person's lungs decreases. By placing two or more electrodes on a user's body around the lungs, the differential voltage ($V_{body}$) across $Z_{body}$ can be measured by a sensor device once again to allow for the calculation of $Z_{body}$. $Z_{body}$ is directly proportional to the air in the lungs per the following equation:

$$\text{Air in Lungs } \alpha Z_{body}.$$

One of ordinary skill in the art readily recognizes that the input voltage signal ($V_{in}$) can be a variety of types of signals including but not limited to a 1 MHz square wave current with amplitude 150 uA, a single ended signal, a differential signal that can be inputted at different locations on the user's body, or a differential signal that can be inputted at different times or simultaneously and that would be within the spirit and scope of the present invention. Additionally, one of ordinary skill in the art readily recognizes that the input voltage signal ($V_{in}$) can be inputted into multiple electrodes which would create multiple differential voltages requiring additional calculations to find $Z_{body}$ and that would be within the spirit and scope of the present invention.

One of ordinary skill in the art readily recognizes that the known impedance ($Z_{in}$) can be a variety of impedances including but not limited to any combination of resistors, capacitors, inductors, switches, and transformer elements either in series or in parallel combinations to form an impedance that is deterministic in nature and that would be within the spirit and scope of the present invention.

To measure $Z_{body}$ more accurately, one of ordinary skill in the art readily recognizes that the input voltage signal ($V_{in}$) can be a high frequency square wave current or a pulsed signal with fast rise and fall times that are less than 50 nanoseconds (ns) to reduce and make negligible the impedance of the two or more electrodes and that would be within the spirit and scope of the present invention.

After measuring the differential voltage or voltage waveform across the two or more electrodes of the sensor device, peaks of the differential voltage are sampled by an analog-to-digital converter. One of ordinary skill in the art readily recognizes that the peaks of the differential voltage can be sampled at a variety of rates including but not limited to 1 Mega Sample per second (MS/s). After the peaks of the differential voltage are sampled, the peaks of the differential voltage are downsampled to 12.5 samples per second or at a sampling rate of 12.5 Hz.

Accordingly, if the differential voltage is downsampled to 12.5 samples per second and it takes roughly 6 seconds per breath, then that would result in 75 samples per breath being sampled. One of ordinary skill in the art readily recognizes that these sampling rates and breath duration values can vary and that would be within the spirit and scope of the present invention.

As aforementioned, after sampling of the resultant electrical output signal, it is then processed to remove noise such as bodily movements or motion artifacts using a variety of hardware and/or software approaches including but not limited to a processing unit with circuits that perform functions such as rectification, absolute value, sample-and-hold, and track-and-hold. The processing unit can be a separate device coupled to the sensor device or can be entirely and/or partially embedded within the sensor device. These circuits may cause transitions or glitches in the output signal produced when the input voltage signal ($V_{in}$) or a circuit clock transitions. One of ordinary skill in the art readily recognizes that a common analog circuit block can be used after these circuits to reduce and/or eliminate the effects of these glitches or transitions and that would be within the spirit and scope of the present invention.

One of ordinary skill in the art readily recognizes that the common analog circuit block can be a variety of devices including but not limited to a filter that suppresses sharp transitions or a sampling circuit that has a clock with correct phase and/or correct duty cycle so the glitches or transitions are not detected by subsequent circuit blocks and that would be within the spirit and scope of the present invention. Additionally, one of ordinary skill in the art readily recognizes that the clock within each circuit block of the processing unit can have a variety of features including but not limited to programmable phase shifts, being phase shifted with respect to one another, and being non-overlapping with respect to one another through phase shifting, duty cycle alterations, or programmability and that would be within the spirit and scope of the present invention.

In addition to the glitches or transitions in the output signal, one of ordinary skill in the art readily recognizes that the processing unit can experience a variety of circuit non-idealities including but not limited to voltage driver pull-up and pull-down impedances and/or transition times being mismatched, a duty cycle of the voltage driver pull-up and pull-down not being ideal, the voltage driver not being completely differential due to a mismatch or by design, offsets in the various circuit blocks, and various circuit clocks being out of phase due to variations or by design and that would be within the spirit and scope of the present invention. These circuit non-idealities can be overcome by performing analog and/or digital processing including but not limited to circuit calibrations, adding switches, and programmatically altering any of the circuit blocks and that would be within the spirit and scope of the present invention.

After the sampling and processing of the resultant electrical output signal, the processed output signal undergoes additional calculations and conditional comparisons to determine whether a breath of the user has been detected. Each voltage cycle measured from a starting point to a subsequent starting point on the voltage waveform corresponds to a breath. One of ordinary skill in the art, readily recognizes that subsequent detected breaths of the user can be utilized to determine the respiratory rate of the user and that would be within the spirit and scope of the present invention.

To describe the features of the present invention in more detail, refer now to the following description in conjunction with the accompanying Figures.

Figure 1:
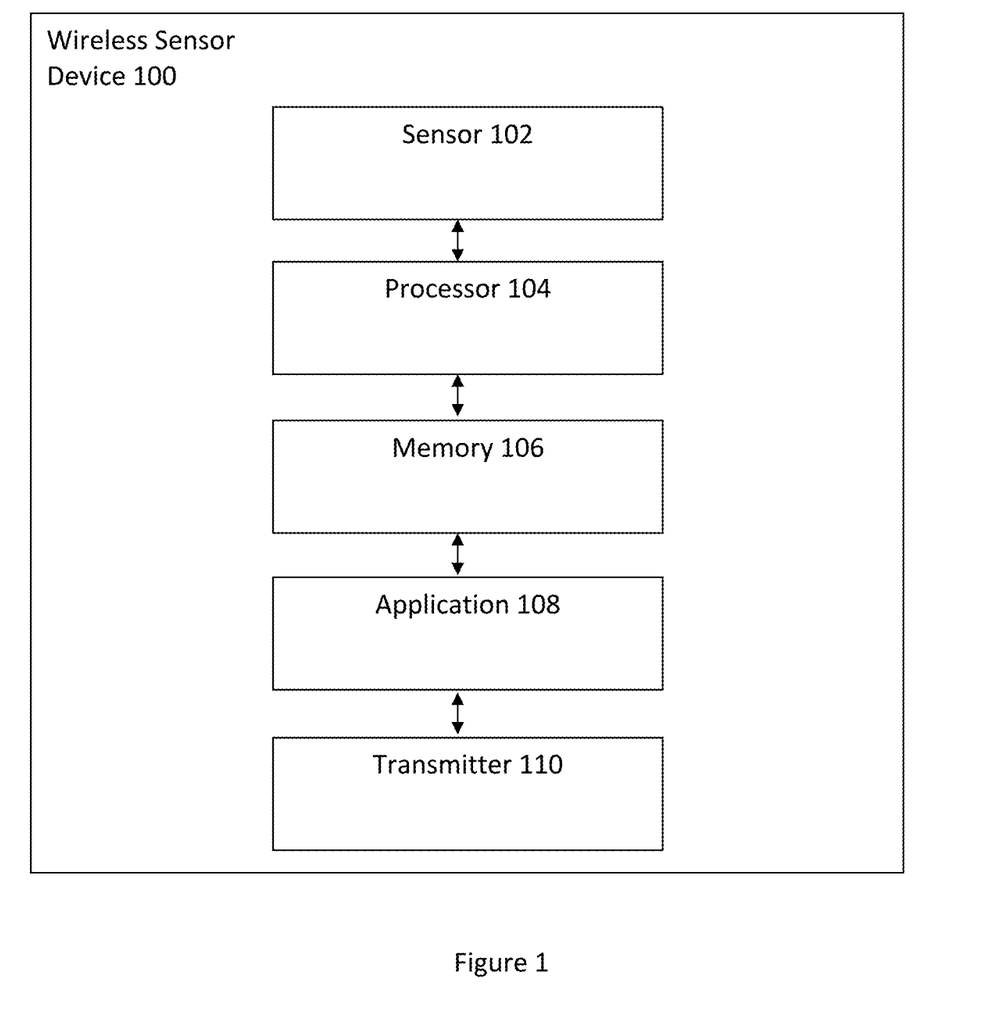
FIG. 1 illustrates a wireless sensor device in accordance with an embodiment.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The wireless sensor device 100 is attached, in any orientation, to a user. The sensor 102 obtains data from the user and transmits the data to the memory 106 and in turn to the application 108. The processor 104 executes the application 108 to determine information regarding whether a user has taken a breath and subsequently determines a respiratory rate of the user. The information is transmitted to the transmitter 110 and in turn relayed to another user or device.

One of ordinary skill in the art readily recognizes that the wireless sensor device 100 can utilize a variety of devices for the sensor 102 including but not limited to uni-axial accelerometers, bi-axial accelerometers, tri-axial accelerometers, gyroscopes, and pressure sensors and that would be within the spirit and scope of the present invention. One of ordinary skill in the art readily recognizes that the wireless sensor device 100 can utilize a variety of devices for the processor 104 including but not limited to microprocessors, controllers, and microcontrollers and that would be within the spirit and scope of the present invention. In addition, one of ordinary skill in the art readily recognizes that a variety of devices can be utilized for the memory 106, the application 108, and the transmitter 110 and that would be within the spirit and scope of the present invention.

Figure 2:
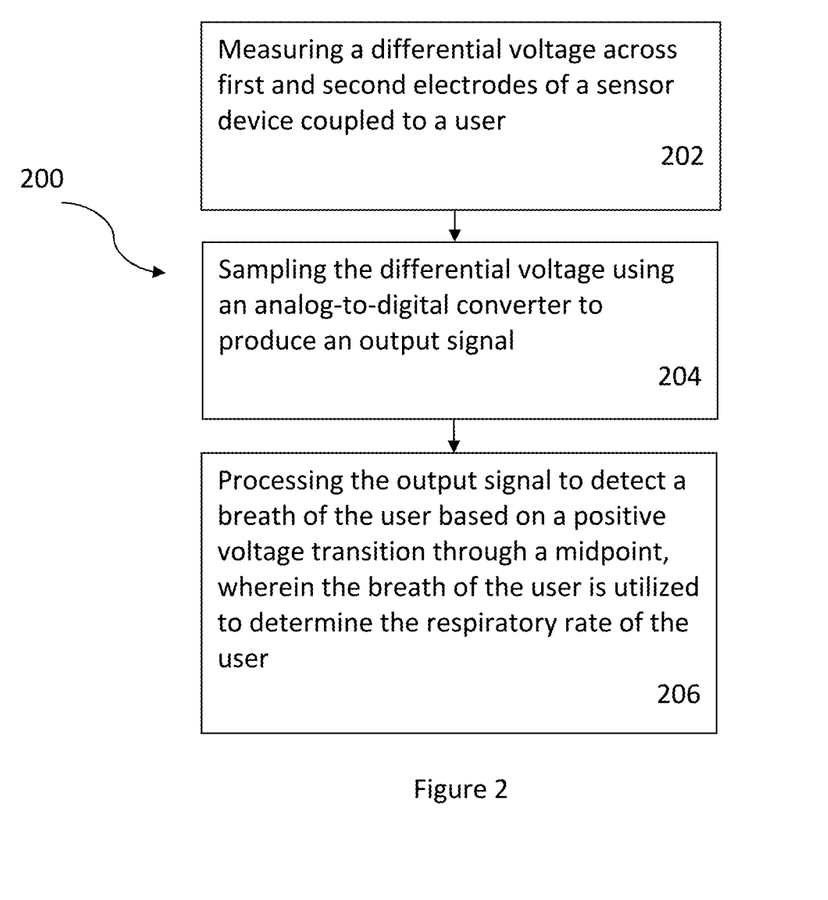
FIG. 2 illustrates a flow chart of a method in accordance with an embodiment.

FIG. 2 illustrates a flow chart of a method 200 in accordance with an embodiment. Referring to FIGS. 1 and 2 together, a differential voltage across first and second electrodes of the wireless sensor device 100 that is coupled to a user is measured by the sensor 102, via step 202. The differential voltage is sampled using an analog-to-digital converter of the wireless sensor device 100 to produce an output signal, via step 204. The output signal is processed by the processor 104 to detect a breath of the user based on a positive voltage transition through a midpoint, wherein the breath of the user is utilized to determine the respiratory rate of the user. One of ordinary skill in the art readily recognizes that a variety of analog-to-digital converters can be utilized to sample the differential voltage and that would be within the spirit and scope of the present invention.

Figure 3:
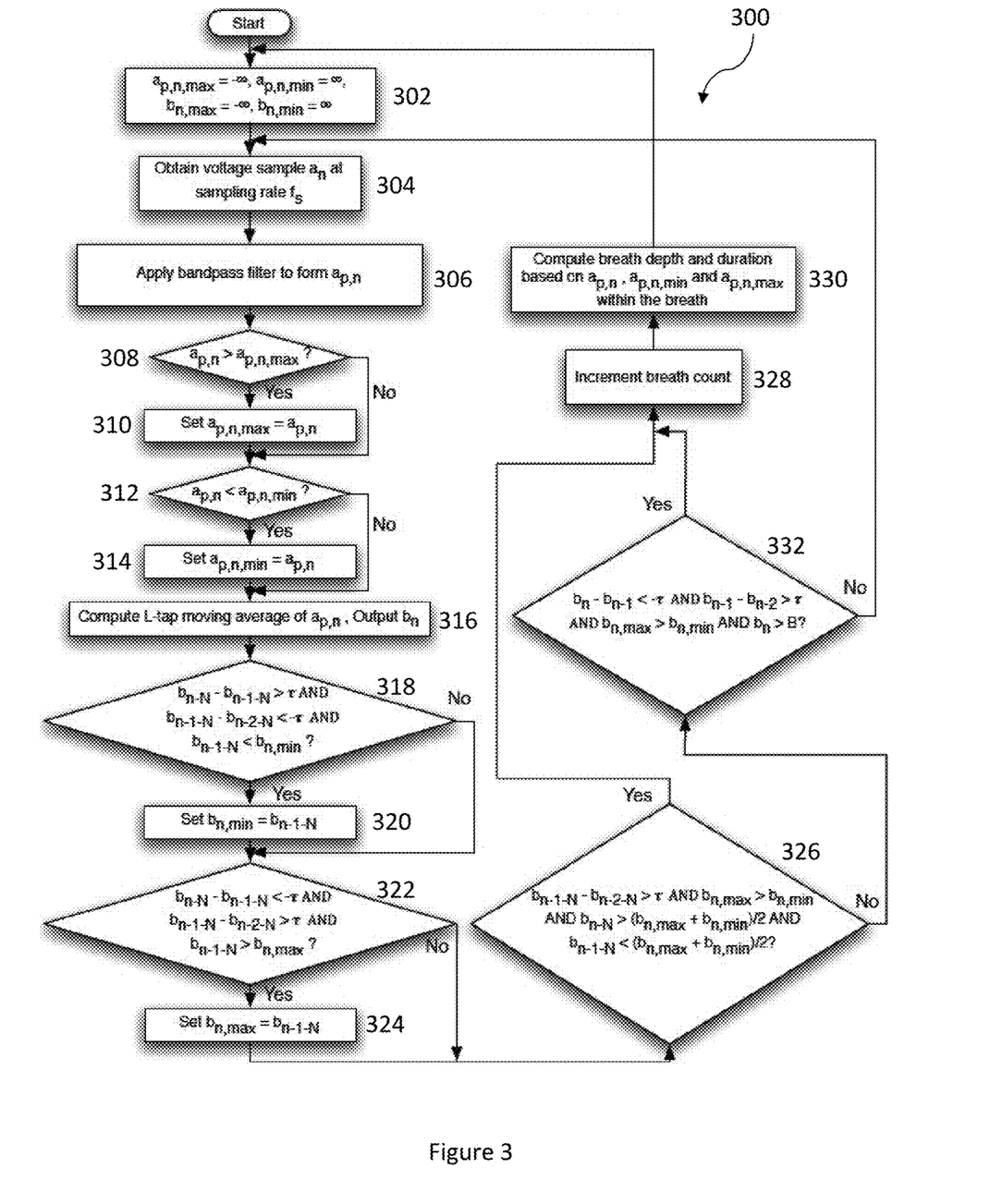
FIG. 3 illustrates a more detailed flow chart of a method in accordance with an embodiment.

FIG. 3 illustrates a more detailed flow chart of a method 300 in accordance with an embodiment. Referring to FIGS. 1 and 2 together, during initialization of the wireless sensor device 100 between each detected breath, system maximum and minimum values are set, via step 302, as follows: $a_{p,n,max}$ is set to $-\infty$, $a_{p,n,min}$ is set to $\infty$, $b_{n,max}$ is set to $-\infty$, and $b_{n,min}$ is set to $\infty$. This ensures that the initial samples that are obtained and processed will override these initialized maximum and minimum values. One of ordinary skill in the art readily recognizes that a variety of suitable finite values can be utilized during initialization instead of $+-\infty$ and that would be within the spirit and scope of the present invention.

After the differential voltage has been measured by the sensor 102 of the wireless sensor device 100, a voltage sample ($a_n$) is obtained at a sampling rate of $f_s$, via step 304. In one embodiment, $f_s$=12.5 samples per second received and stored in the memory 106 while only one voltage sample ($a_n$) at a time runs through the rest of the method 300. One of ordinary skill in the art readily recognizes that a variety of sampling rates can be utilized including but not limited to 12.5 Hz and that would be within the spirit and scope of the present invention.

A bandpass filter (BPF) is applied to the voltage sample ($a_n$) reduce motion artifacts thereby outputting an output signal ($a_{p,n}$), via step 306. The BPF further reduces noise and outputs a smoother output signal. In one embodiment, the BPF is a second order Butterworth filter with a passband from 0.06 to 1.1 Hz. One of ordinary skill in the art readily recognizes that the passband can be a variety of ranges including but not limited to a range in accordance with respiratory physiology with the assumption that typical respiratory rate values range from 6 breaths per minute (or 10 seconds per breath) to 24 breaths per minute and that would be within the spirit and scope of the present invention.

The method 300 compares whether the output signal ($a_{p,n}$) is greater than $a_{p,n,max}$, via step 308. If yes, then $a_{p,n,max}$ is set to $a_{p,n}$ which overrides the stored maximum value, via step 310, and the method 300 moves to step 312. If no, the method 300 compares whether the output signal ($a_{p,n}$) is less than $a_{p,n,min}$, via step 312. If yes, then $a_{p,n,min}$ is set to $a_{p,n}$ which overrides the stored minimum value, via step 314, and the method 300 moves to step 316. If no, the method 300 moves to step 316.

One of ordinary skill in the art readily recognizes that when the output signal ($a_{p,n}$) is the first sample that is running through the method 300, that this first sample value will be greater than $a_{p,n,max}$ and less than $a_{p,n,min}$ and so the first sample value always overrides the initialized maximum and minimum values and that would be within the spirit and scope of the present invention.

A finite impulse response (FIR) filter is applied to the output signal ($a_{p,n}$) to compute an L-tap moving average of the output signal ($a_{p,n}$) to further smooth the signal thereby outputting an output signal ($b_n$), via step 316. One of ordinary skill in the art readily recognizes that a variety of tap values can be utilized by the FIR filter including but not limited to where L=6 and that would be within the spirit and scope of the present invention.

In the method 300, the voltage samples ($a_n$) and averaged output signal values ($b_n$) are stored in the memory 106. The stored samples are used after delays of a predetermined number of samples (N) before proceeding with the conditional calculations that lead to the detection of a breath of the user. One of ordinary skill in the art readily recognizes that the delay of a predetermined number of samples can be a variety of values including but not limited to N=20 and that would be within the spirit and scope of the present invention.

A breath is detected after a delay of a predetermined number of samples (N=20) at a positive crossing or voltage transition of a midpoint value between minimum ($b_{n,min}$) and maximum ($b_{n,max}$) values of $b_n$ at each breathing cycle, wherein the minimum ($b_{n,min}$) and maximum ($b_{n,max}$) values of $b_n$ are taken over all samples in each breathing cycle. Detecting the breath using midpoint detection rather than peak detection reduces the impact of motion artifacts. To determine the minimum value ($b_{n,min}$), the method 300 calculates whether the following conditions are satisfied, via step 318:

$$(b_{n-N})-(b_{n-1-N}) > \text{hysteresis threshold (tau)} \quad (1)$$

$$(b_{n-2-N})-(b_{n-1-N}) > \text{hysteresis threshold (tau)} \quad (2)$$

$$b_{n-1-N} < b_{n,min} \quad (3)$$

If all three of these conditions ((1)-(3)) are satisfied because $b_{n-1-N}$ is determined to be smaller than $b_{n-N}$ and $b_{n-N-2}$, then the minimum value ($b_{n,min}$) is set as $b_{n-1-N}$ thus overriding previously set values, via step 320, and the method moves to step 322 to determine the maximum value ($b_{n,max}$). One of ordinary skill in the art readily recognizes that the hysteresis threshold (tau) can be a variety of values including but not limited to tau=0.08 mV and that would be within the spirit and scope of the present invention. If all three of these conditions ((1)-(3)) are not satisfied, then the method moves to step 322 to determine the maximum value ($b_{n,max}$).

To determine the maximum value ($b_{n,max}$), the method 300 calculates whether the following conditions are satisfied, via step 322:

$$(b_{n-1-N})-(b_{n-N}) > \text{hysteresis threshold (tau)} \quad (4)$$

$$(b_{n-1-N})-(b_{n-2-N}) > \text{hysteresis threshold (tau)} \quad (5)$$

$$b_{n-1-N} > b_{n,max} \quad (6)$$

If all three of these conditions ((4)-(6)) are satisfied because $b_{n-1-N}$ is determined to be greater than $b_{n-N}$ and $b_{n-N-2}$, then the maximum value ($b_{n,max}$) is set as $b_{n-1-N}$ thus overriding previously set values, via step 324, and the method moves to step 326 to determine the midpoint value. If all three of these conditions ((4)-(6)) are not satisfied, then the method moves to step 326 to determine the midpoint value.

To determine the positive voltage transition through the midpoint value and detect a breath of the user, the method 300 calculates whether the following conditions are satisfied, via step 326:

$$(b_{n-1-N}) - (b_{n-2-N}) > \text{hysteresis threshold (tau)} \quad (7)$$

$$b_{n,max} > b_{n,min} \quad (8)$$

$$b_{n-N} > (b_{n,max} + b_{n,min})/2 \quad (9)$$

$$b_{n-1-N} > (b_{n,max} + b_{n,min})/2 \quad (10)$$

The conditions verify that the samples are transitioning in a positive direction and from below the midpoint value to above the midpoint value. If all four of these conditions ((7)-(10)) are satisfied, then a breath of the user is detected and the method 300 increments the breath count, via step 328. If all four of these conditions ((7)-(10)) are not satisfied, and a breath is not detected (e.g. because of the user's breathing change from deep to shallow breathing), then the method 300 moves to step 332 to detect a breath at a local maximum above a predetermined threshold (B). One of ordinary skill in the art readily recognizes that the predetermined threshold (B) can be a variety of values including but not limited to a function of $b_{n,min}$ and $b_{n,max}$ such as B=constant*$b_{n,min}$, B=constant+$b_{n,min}$, and B=$(3b_{n,min} + b_{n,max})/4$ and that would be within the spirit and scope of the present invention.

One of ordinary skill in the art readily recognizes that these examples of the threshold B are chosen such that the local maximum of a shallow breath after a deep breath can be detected and that would be within the spirit and scope of the present invention. For example, the threshold B= $(3b_{n,min} + b_{n,max})/4$ allows a local maximum from a shallow breath to be detected even if that local maximum is below the midpoint between the previous breath's maximum and minimum values.

To detect a breath at the local maximum above the predetermined threshold (B), the method 300 calculates whether the following conditions are satisfied, via step 332:

$$(b_{n-1}) - (b_n) > \text{hysteresis threshold (tau)} \quad (11)$$

$$(b_{n-1}) - (b_{n-2}) > \text{hysteresis threshold (tau)} \quad (12)$$

$$b_{n,max} > b_{n,min} \quad (13)$$

$$b_n > B \quad (14)$$

Figure 4:
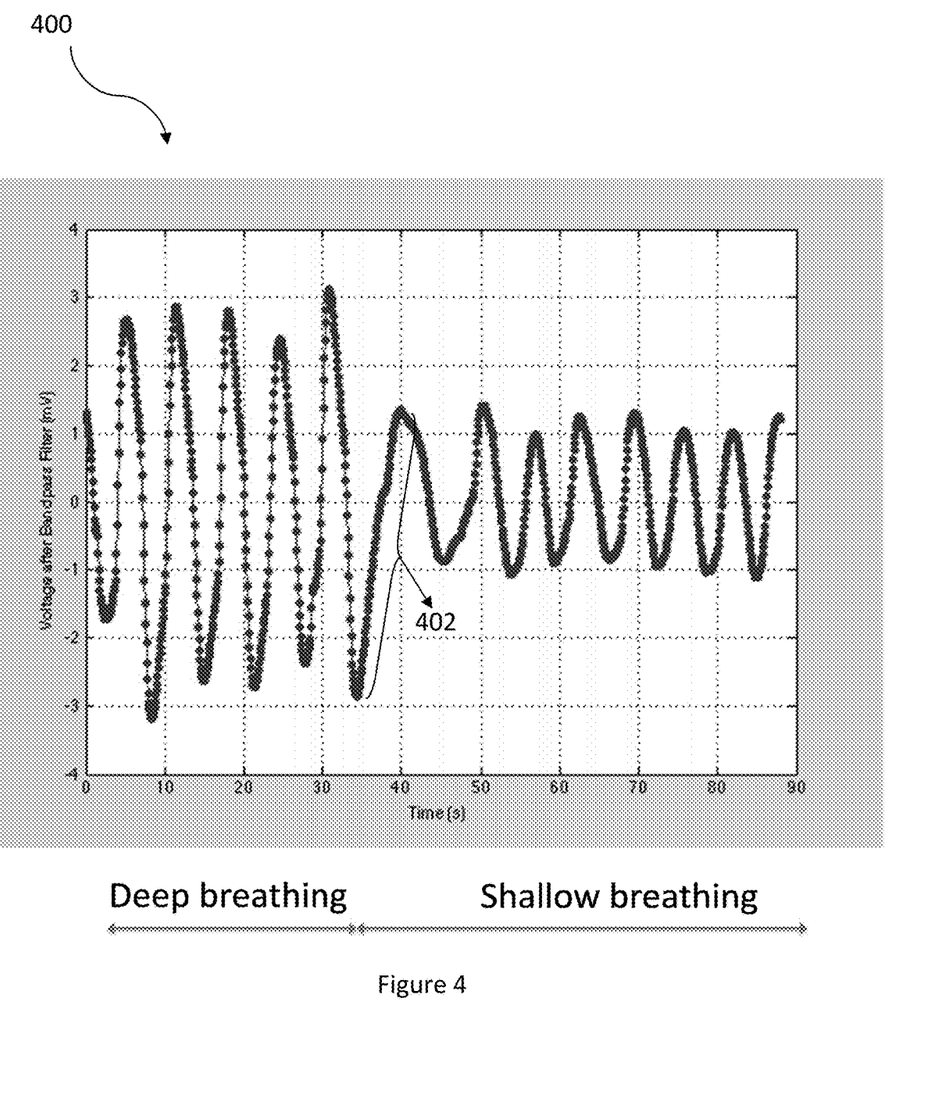
FIG. 4 illustrates a graphical chart in accordance with an embodiment.

The conditions verify that $b_n$ does not fall in between a transition period that embodies the period between the last section of the deep breathing and the first section of the shallow breathing. FIG. 4 illustrates a graphical chart 400 in accordance with an embodiment. The graphical chart 400 displays a transition period 402 in between a period of deep breathing and a period of shallow breathing where a breath would not be detected by the method 300 because all four of these conditions ((11)-(14)) are not satisfied.

If all four of these conditions ((11)-(14)) are satisfied, then a breath of the user has been detected and the method 300 increments the breath count, via step 328. If all four of these conditions ((11)-(14)) are not satisfied, and a breath is not detected, then the method 300 returns back to step 304 to obtain additional voltage samples and continue to run through steps 306-332.

After detecting a breath of the user and incrementing the breath counter, the method 300 computes breath depth and duration, via step 330, and returns back to step 302 to re-initialize the wireless sensor device 100. In one embodiment, the breath depth is computed by comparing $a_{p,n,min}$ and $a_{p,n,max}$ values of a breath cycle. In one embodiment, the breath duration is computed by comparing similar starting and ending points of consecutive breaths (e.g. $a_{p,n}$ of breath $m_1$ and $p_{p,n}$ of breath $m_2$) and measuring the time value in between each of the consecutive breaths. One of ordinary skill in the art readily recognizes that the starting and ending points can be a variety of points including but not limited to peak values, minimum values, and midpoint values of each breath cycle and that would be within the spirit and scope of the present invention.

In one embodiment, to calculate the respiratory rate of the user, two consecutive breaths ($m_1$ and $m_2$) that have been detected by the method 300 are utilized. The time period in seconds ($T_m$) in between consecutive breaths $m_1$ and $m_2$ is compared to a minimum time period value ($T_{min}$). If $T_m < T_{min}$ then the breath $m_2$ is ignored and the method 300 tries to detect another breath $m_3$ to utilize for the respiratory rate determination. One of ordinary skill in the art readily recognizes that $T_{min}$ can be a variety of lower threshold values including but not limited to 0.67 seconds that are utilized to ignore certain breath detections and that would be within the spirit and scope of the present invention.

If $T_m > T_{min}$, then an instantaneous respiratory rate ($R_m$) is calculated per the equation $R_m = 60/T_m$. Another lowpass filter can be applied to this calculated $R_m$ to further reduce noise and/or artifacts and the output is rounded to a nearest integer and the resulting output is reported as the respiratory rate of the user in breaths per minute. One of ordinary skill in the art readily recognizes that a lowpass filter does not have to be applied to report the respiratory rate of the user and that a variety of filters can be utilized including but not limited to a lowpass filter with a moving average of length 4 and that would be within the spirit and scope of the present invention. In another embodiment, a lowpass filter is applied to $T_m$ to result in a filtered output that is used to compute $R_m$ according to the aforementioned relation $R_m = 60/T_m$.

Additionally, from the detection of the breaths from the method 300, one of ordinary skill in the art readily recognizes that a variety of other calculations can be utilized to determine the respiratory rate of the user and that would be within the spirit and scope of the present invention.

As above described, the method and system allow for respiratory rate of a user using a sensor device. By inputting a voltage signal through known impedances and into a sensor device that has been placed on a location of the body (e.g. torso) of a user, detecting the resultant output voltage signal, and processing the resultant output voltage using a combination of analog and digital signal processing, an accurate respiratory rate can be calculated utilizing a non-invasive and efficient system.

A method and system for determining a respiratory rate of a user has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for continuous monitoring of a respiratory rate of a user using a wearable sensor device, wherein the wearable sensor device comprises a memory, a processing unit coupled to the memory and executing instructions stored therein, an analog-to-digital converter coupled to the memory, a transmitter coupled to the memory and first and second electrodes coupled to the analog-to-digital converter and the method comprising:
    measuring a differential voltage across the first and second electrodes of the wearable sensor device coupled to the user, wherein a voltage signal of known impedance is used as an input signal;
    sampling the measured differential voltage using the analog-to-digital converter to produce an output signal; and
    detecting a breath of the user, wherein detecting the breath comprises:
        determining a local maximum using the output signal,
        determining transitioning of the samples from below a midpoint value to above the midpoint value using the output signal, when the local maximum of the output signal is above a midpoint between maximum value of previous breath and minimum value of previous breath, wherein a positive voltage transition through the midpoint indicates the breath of the user, and
        comparing the local maximum with a predetermined threshold when the local maximum of the output signal is below the midpoint between the previous breath's maximum and minimum value, wherein the local maximum above the predetermined threshold indicates the breath of the user;
    wherein the breath of the user is utilized to determine the respiratory rate of the user, which is transmitted to another user or device by the transmitter.

2. The method of claim 1, further comprising:
    applying a voltage signal to the first and the second electrodes, wherein the voltage signal is a high frequency square wave or a pulse signal with rise and fall times such that an impedance of the first and second electrodes is lower than a body impedance.

3. The method of claim 1, wherein the sampling further comprises:
    sampling peaks of the differential voltage; and
    downsampling the sampled peaks to provide a voltage sample ($a_n$) as the output signal.

4. The method of claim 3, wherein the peaks of the differential voltage are sampled at 1 mega sample per second (MS/s) and the sampled peaks are downsampled to 12.5 samples per second.

5. The method of claim 1, wherein the processing further comprises:
    applying a first filter to the output signal to remove any of noise and artifacts thereby producing a second output signal ($a_{p,n}$); and
    applying a second filter to the second output signal ($a_{p,n}$) to compute an L-tap moving average of the second output signal thereby producing a third output signal ($b_n$).

6. The method of claim 5, wherein the first filter is a second order Butterworth filter with a passband from 0.06 Hertz (Hz) to 1.1 Hz and the second filter is a finite impulse response (FIR) filter where L=6.

7. The method of claim 5, wherein the midpoint is a midpoint between maximum ($b_{n,max}$) and minimum ($b_{n,min}$) values of the third output signal ($b_n$).

8. The method of claim 7, wherein the minimum value ($b_{n,min}$) is set to $b_{n-1-N}$ when the following conditions are satisfied:

$(b_{n-N})-(b_{n-1-N})>$hysteresis threshold (tau);

$(b_{n-2-N})-(b_{n-1-N})>$hysteresis threshold (tau); and $b_{n-1-N}<b_{n,min}.$ 9. The method of claim 7, wherein the maximum value ($b_{n,max}$) is set to $b_{n-1-N}$ when the following conditions are satisfied:

$(b_{n-1-N})-(b_{n-N})>$hysteresis threshold (tau);

$(b_{n-1-N})-(b_{n-2-N})>$hysteresis threshold (tau); and $b_{n-1-N}>b_{n,max}.$ 10. The method of claim 9, further comprising:
    waiting a predetermined time period (N) before calculating the positive voltage transition through the midpoint, wherein the breath of the user is detected when the following conditions are satisfied:

$(b_{n-1-N})-(b_{n-2-N})>$hysteresis threshold (tau);

$b_{n,max}>b_{n,min};$ $b_{n-N}>(b_{n,max}+b_{n,min})/2;$ and $b_{n-1-N}>(b_{n,max}+b_{n,min})/2.$ 11. The method of claim 5, further comprising:
    calculating breath depth by using minimum ($a_{p,n,min}$) and maximum ($a_{a,p,max}$) values of the second output signal ($a_{p,n}$); and
    calculating breath duration by comparing time values of the second output signal ($a_{p,n}$ for breath $m_2$) and a preceding second output signal ($a_{p,n}$ for breath $m_1$).

12. A system for continuous monitoring a respiratory rate of a user using a wearable sensor device, the system comprising:
    the wearable sensor device comprising a memory, a processing unit coupled to the memory and executing instructions stored therein, a transmitter coupled to the memory and first and second electrodes coupled to the user, wherein a voltage signal of known impedance is used as an input signal, and wherein the wearable sensor device measures a differential voltage across the first and the second electrodes; and an analog-to-digital converter coupled to the first and second electrodes of the wearable sensor device, wherein the analog-to-digital converter samples the differential voltage measured by the first and second electrodes to produce an output signal;

wherein the processing unit coupled to the wearable sensor device processes the output signal to detect a breath of the user by executing instructions comprising:

determine a local maximum using the output signal, determine transitioning of the samples from below a midpoint value to above the midpoint value using the output signal, when the local maximum of the output signal is above a midpoint between maximum value of previous breath and minimum value of previous breath, wherein a positive voltage transition through the midpoint indicates the breath of the user; and compare the local maximum with a predetermined threshold when the local maximum of the output signal is below the midpoint between the previous breath's maximum and minimum value, wherein the local maximum above the predetermined threshold indicates the breath of the user;

wherein the breath of the user is utilized to determine the respiratory rate of the user, which is transmitted to another user or device by the transmitter.

13. The system of claim 12, further comprising:

a voltage generator coupled to the wearable sensor device, wherein the voltage generator applies a voltage signal to the first and the second electrodes, wherein the voltage signal is a high frequency square wave or a pulse signal with rise and fall times such that an impedance of the first and second electrodes is lower than a body impedance.

14. The system of claim 12, wherein the analog-to-digital converter further:

samples peaks of the differential voltage; and downsamples the sampled peaks to provide a voltage sample ($a_n$) as the output signal.

15. The system of claim 14, wherein the peaks of the differential voltage are sampled at 1 mega sample per second (MS/s) and the sampled peaks are downsampled to 12.5 samples per second.

16. The system of claim 12, wherein the wearable sensor device further:

applies a first filter to the output signal to remove any of noise and artifacts which produces a second output signal ($a_{p,n}$); and applies a second filter to the second output signal ($a_{p,n}$) to compute an L-tap moving average of the second output signal which produces a third output signal ($b_n$).

17. The system of claim 16, wherein the midpoint is a midpoint between maximum ($b_{n,max}$) and minimum ($b_{n,min}$) values of the third output signal ($b_n$).

18. The system of claim 17, wherein the wearable sensor device further:

waits a predetermined time period (N) before calculating the positive voltage transition through the midpoint, wherein the breath of the user is detected when the following conditions are satisfied:

$(b_{n-1-N}) - (b_{n-2-N}) >$ hysteresis threshold (tau);

$b_{n,max} > b_{n,min}$;

$b_{n-N} > (b_{n,max} + b_{n,min})/2$; and $b_{n-1-N} > (b_{n,max} + b_{n,min})/2$.

* * * * *